United States Patent
Rosiello

(10) Patent No.: US 7,993,310 B2
(45) Date of Patent: Aug. 9, 2011

(54) COLLECTION NEEDLE

(75) Inventor: Keith M. Rosiello, Shrewsbury, MA (US)

(73) Assignee: Velico Medical, Inc., Beverly, MA (US)

(*) Notice: Subject to any disclaimer, the term of this patent is extended or adjusted under 35 U.S.C. 154(b) by 0 days.

(21) Appl. No.: 11/798,915

(22) Filed: Apr. 13, 2007

(65) Prior Publication Data

US 2008/0103458 A1 May 1, 2008

Related U.S. Application Data

(62) Division of application No. 10/211,144, filed on Aug. 2, 2002, now Pat. No. 7,204,828.

(60) Provisional application No. 60/322,400, filed on Sep. 14, 2001.

(51) Int. Cl.
- *A61M 5/32* (2006.01)
- *A61M 31/00* (2006.01)
- *A61B 10/00* (2006.01)

(52) U.S. Cl. .................. 604/272; 604/506; 600/564

(58) Field of Classification Search .......... 604/272–274, 604/500–522; 600/564
See application file for complete search history.

(56) References Cited

U.S. PATENT DOCUMENTS

| | | | |
|---|---|---|---|
| 2,512,569 A * | 6/1950 | Saffir | |
| 3,492,992 A * | 2/1970 | Kurtz | |
| 4,002,174 A * | 1/1977 | Reed et al. | |
| 4,098,275 A * | 7/1978 | Consalvo | |
| 4,134,402 A * | 1/1979 | Mahurkar | |
| 4,180,068 A * | 12/1979 | Jacobsen et al. | |
| 4,308,875 A * | 1/1982 | Young | 600/566 |
| 4,537,593 A * | 8/1985 | Alchas | |
| 4,675,004 A * | 6/1987 | Hadford et al. | |
| 4,816,018 A * | 3/1989 | Parisi | |
| 5,152,744 A * | 10/1992 | Krause et al. | |
| 5,254,106 A * | 10/1993 | Feaster | |
| 5,300,084 A * | 4/1994 | Johnson | |

(Continued)

FOREIGN PATENT DOCUMENTS

DE 195 12 607 A1 * 10/1996

(Continued)

OTHER PUBLICATIONS

International Search Report date of mailing Nov. 28, 2002.

*Primary Examiner* — Theodore J Stigell
*Assistant Examiner* — Imani Hayman
(74) *Attorney, Agent, or Firm* — Foley & Lardner LLP; Michel Morency; Matthew L. Fenselau

(57) ABSTRACT

A needle structure having proximal and distal ends and including a collection needle section at a more proximal end of the needle structure and a skin plug retainer section at the very distal end and integral with the collection needle section. The collection needle section includes a generally hollow tubular member having an external surface, an inner lumen and a port through the tubular member so as to enable fluid flow from about the tubular member to the inner lumen for collection therefrom. The skin plug retainer section includes a hollow tubular piece having an external surface and an inner lumen. The hollow tubular piece is beveled at its distal end to form a needle tip. A barrier wall may be disposed intermediate the collection needle section and the skin plug retainer section.

14 Claims, 5 Drawing Sheets

U.S. PATENT DOCUMENTS

| | | | |
|---|---|---|---|
| 5,662,619 A | * | 9/1997 | Zarate |
| 5,868,721 A | * | 2/1999 | Marinacci et al. |
| 5,935,096 A | * | 8/1999 | Barrett |
| 5,976,114 A | * | 11/1999 | Jonkman et al. |
| 6,086,543 A | * | 7/2000 | Anderson et al. ............. 600/567 |
| 6,346,095 B1 | * | 2/2002 | Gross et al. |
| 6,620,139 B1 | * | 9/2003 | Plicchi et al. |
| 6,626,884 B1 | * | 9/2003 | Dillon et al. .................. 604/409 |
| 2004/0116879 A1 | * | 6/2004 | Mascitelli et al. |

FOREIGN PATENT DOCUMENTS

EP            1 036 571 A  *  9/2000

\* cited by examiner

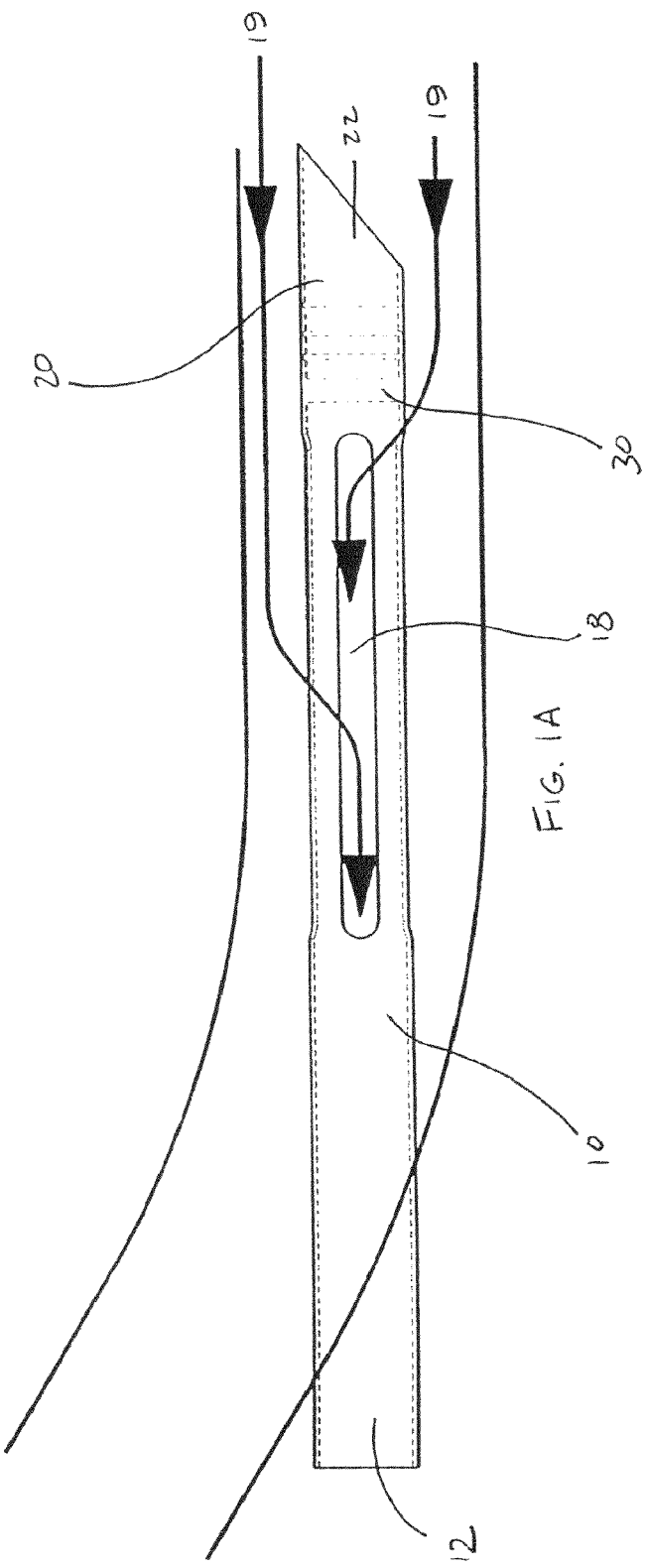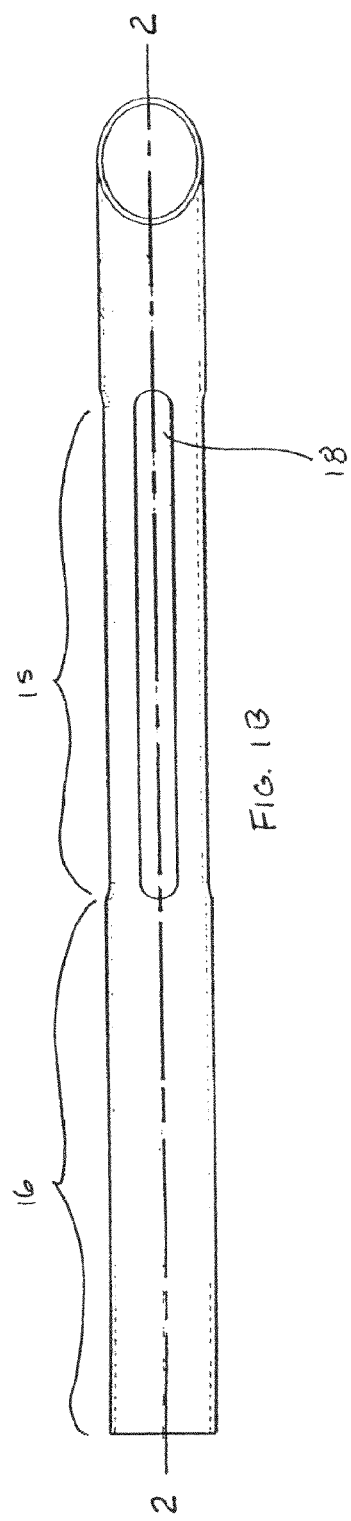

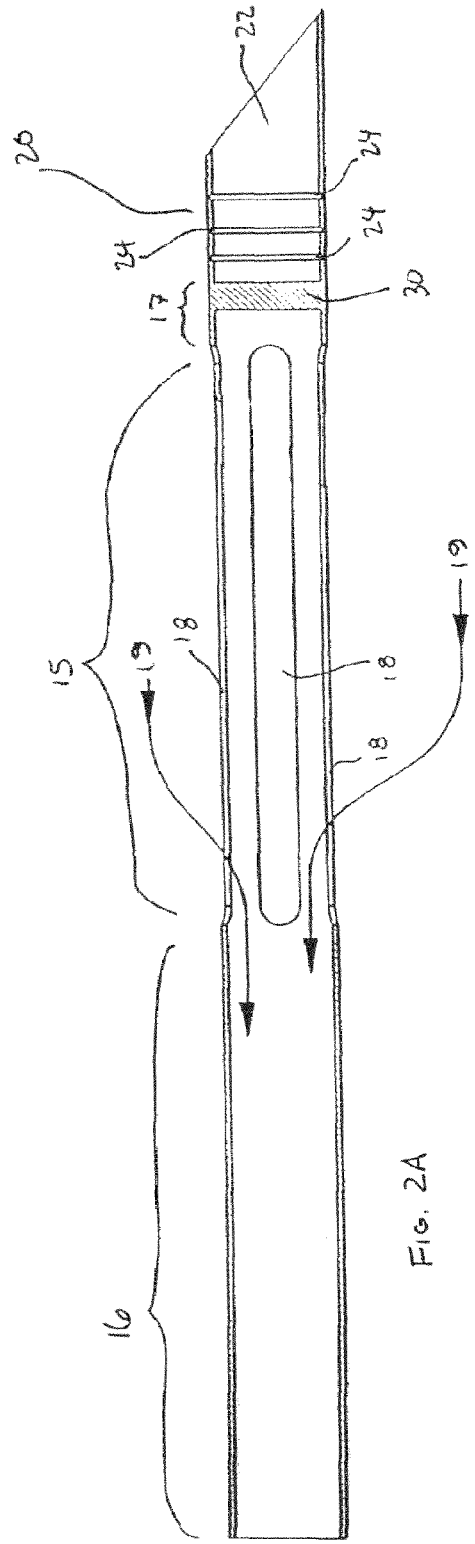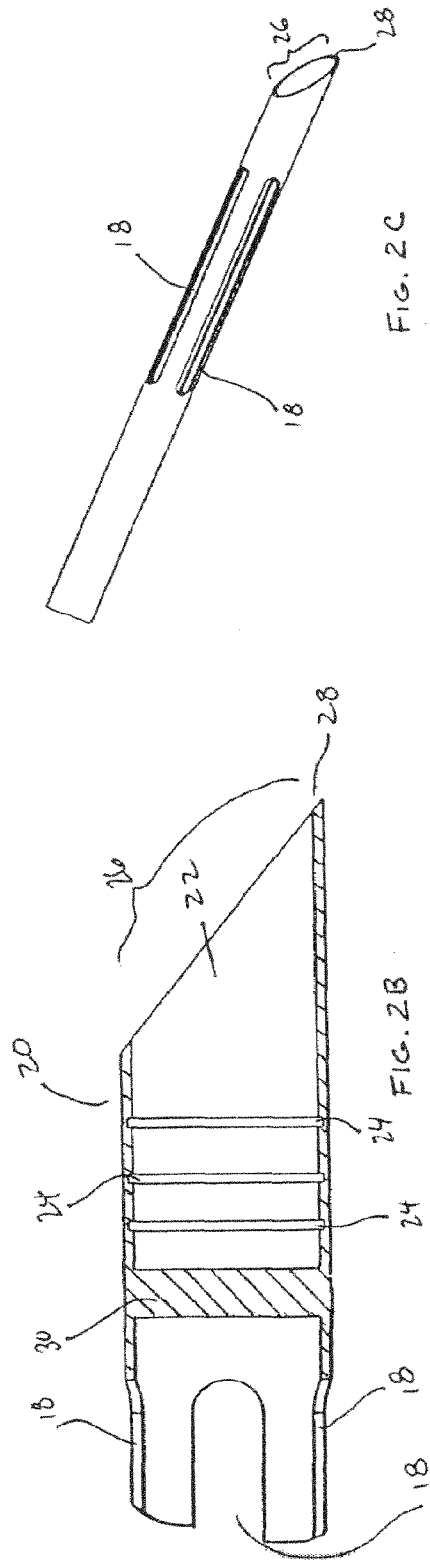

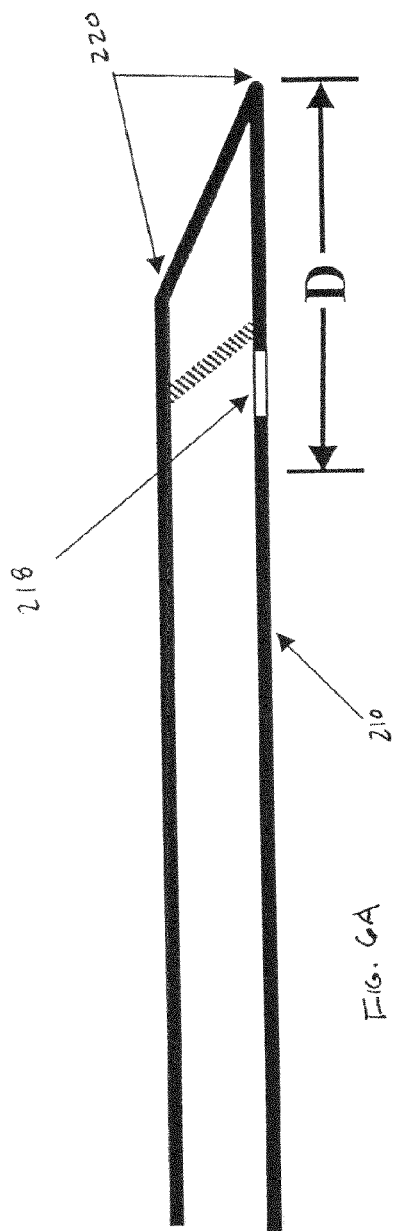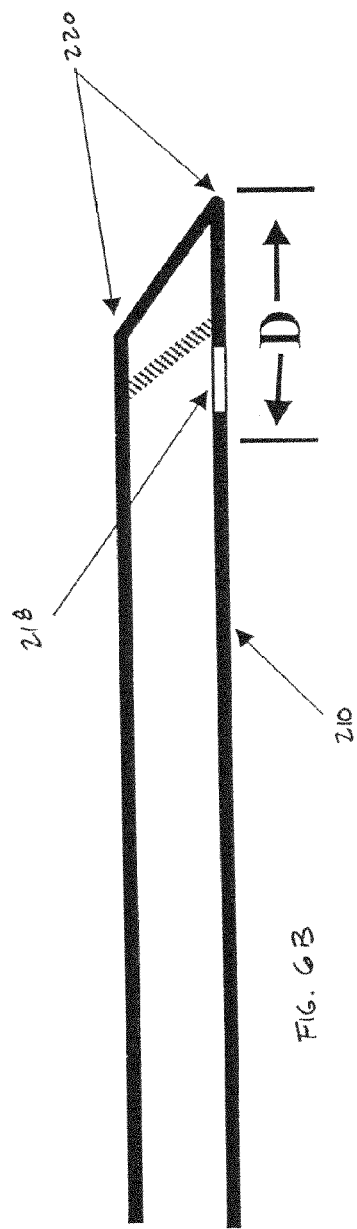

COLLECTION NEEDLE

This application is a divisional of U.S. Patent application Ser. No. 10/211,144, filed Aug. 2, 2002, which claims the benefit of priority of U.S. Provisional Patent Application No. 60/322,400, filed Sep. 14, 2001, the entire disclosure of which is being incorporated herein by reference.

BACKGROUND OF THE INVENTION

1. Field of the Invention

The present invention relates in general to hollow needles such as hypodermic needles, and pertains, more particularly to, an improved needle structure that can be used in the normal manner for fluid injection or collection, in combination with an integral skin plug retainer.

2. The Prior Art

There is a considerable amount of prior art directed to needles and cannulas. The hypodermic needle is one of the basic tools of the medical profession and typically includes a relatively thin, straight, hollow tube that may be coupled at one end to a syringe of one type or another. The other end is usually beveled to provide a sharp point for piercing the skin.

Some of the prior art patents address the issue of minimizing tissue coring, as well as minimizing plugging of the skin. However, the prior art does not discloses a needle structure that is constructed and arranged in combination with an integral skin plug retainer.

For example:
- U.S. Pat. No. 4,383,530 to Bruno described a hypodermic needle with the leading tip at the needle point shielding at least a portion of the hollow needle tube so as to reduce tissue coring;
- U.S. Pat. No. 4,753,641 to Vaslow describes an emergency medical needle employing a jaw structure so as to reduce coring;
- U.S. Pat. No. 5,290,267 to Zimmermann also describes a modified needle structure with an end section that is bent laterally and a hook-shaped curve section, with the structure allegedly to avoid the cutting of plugs during its use; and
- U.S. Pat. No. 5,733,266 to Gravlee Jr. describes a hypodermic needle with a rounded trailing cutting edge for preventing plug cutting.

Accordingly, none of this prior art describes a needle structure that can be used in a normal manner for fluid injection or collection, in combination with an integral skin plug retainer.

SUMMARY OF THE INVENTION

In accordance with the present invention there is provided a needle structure that has proximal and distal ends. This needle structure comprises a needle section that is at a more proximal end of the structure, and a skin plug retainer section at the distal end of the structure and integral with the needle section. In the preferred embodiment described herein, the needle section is a collection needle section. However, it is understood that the principle of the present invention may also be applied in connection with needles for injection into the body, such as different types of hypodermic needles. The collection needle section includes a generally hollow tubular member having an external surface, an inner lumen, and a port through the tubular member so as to enable fluid flow from about the tubular member to the inner lumen for collection therefrom. The skin plug retainer section includes a hollow tubular piece having an external surface and an inner lumen. The hollow tubular piece is preferably beveled at its distal end so as to form a piercing point. A barrier wall may be provided disposed intermediate the collection needle section and the skin plug retainer section. This barrier wall assists in the retention of the skin plug and also blocks fluid flow so that it does not occur over the skin plug.

In accordance with still further aspects of the present invention the hollow tubular piece is cylindrically truncated so as to form a leading tip segment with the aforementioned piercing point. The skin plug retainer may include a retaining member in the inner lumen of the hollow tubular piece. This retaining member may comprise at least one internally disposed annular ridge for retaining a skin plug. In the disclosed embodiment a plurality of such annular ridges are employed. The annular ridges may be disposed in space parallel planes.

In accordance with other aspects of the present invention the collection needle section may include a plurality of ports. The collection needle has a generally longitudinal axis and the port is preferably of elongated configuration extending in the direction of the longitudinal axis. The collection needle section maybe comprised of a plurality of such elongated ports. The ports may be disposed in parallel but spaced one from the next. In one embodiment four such ports are employed disposed about the structure at 90° intervals.

In accordance with still further aspects of the invention the collection needle section may have a stepped portion transitioning between a smaller diameter segment more proximate to the barrier wall and a larger diameter segment more remote from the barrier wall. The large diameter segment is contiguous with the port segment. The gauge of the respective sections may be any convenient size, e.g., 22 ga for the smaller diameter segment more proximate to the barrier wall and 16 ga for the larger diameter segment more remote from the barrier wall. This advantageously allows for a smaller entry point and a larger flow (i.e., in the larger diameter segment). The barrier wall is preferably solid so as to block fluid flow directly between the skin plug retainer section inner lumen and the collection needle section inner lumen.

There is also provided in accordance with the present invention, a method of injecting or collecting a fluid through the skin by means of a needle structure. This method comprises the steps of: providing at the distal end of the needle structure a skin plug retainer section having a retaining lumen and that is integral with a more proximal fluid flow section having a lumen through which a fluid is enabled to flow; penetrating the skin with the needle structure so as to capture a skin plug at the distal end of the needle structure in the skin plug retaining section; and substantially concurrently with the step of penetrating, enabling the fluid flow through the fluid flow section lumen. Preferably, the fluid flow occurs directly with the fluid flow section and is inhibited between the lumens of the fluid flow section and skin plug retaining section. The step of enabling the fluid flow includes inhibiting the fluid flow past the retained skin plug.

BRIEF DESCRIPTION OF THE DRAWINGS

Numerous other features and advantages should now become apparent upon a reading of the following detailed description, taken in conjunction with the accompanying drawings in which:

FIG. 1A is a top plan view of a needle structure of the present invention, showing blood flow into the needle structure upon insertion of the needle into a vein;

FIG. 1B is a side-plan view of the needle structure of the present invention illustrated in FIG. 1A.

FIG. 2A is a detailed cross-sectional view as taken along line 2-2 of FIG. 1 of the needle structure of FIG. 1;

FIG. 2B is an enlarged, cross-sectional view of the plug retaining section of FIG. 2A;

FIG. 2C is a perspective view of the needle structure of FIG. 2A according to the present invention;

FIG. 6A illustrates a cross-sectional view of a first design of a third embodiment of a needle according to the present invention.

FIG. 6B illustrates a cross-sectional view of a second design of a third embodiment of a needle according to the present invention.

DETAILED DESCRIPTION OF THE PREFERRED EMBODIMENTS

Figure 3:
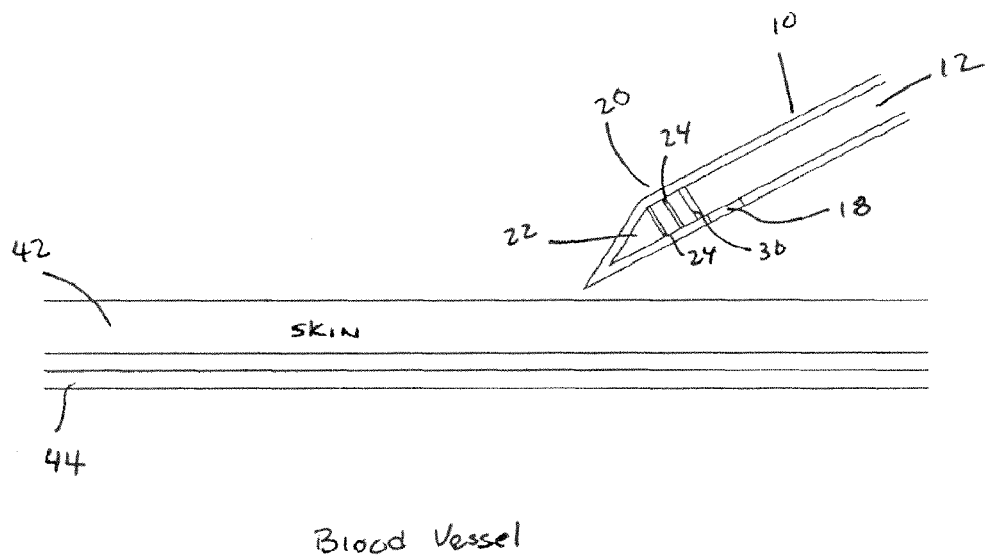
FIG. 3 illustrates the needle structure of the present invention in association with a skin layer before skin penetration.

There is now described herein a collection needle embodying the principles of the present invention. It is understood that the principles of the present invention may also be employed in connection with other types of needles, including hypodermic needles whether for the purpose of collecting a fluid or injecting a fluid. In the embodiment disclosed herein, there is integrated a skin plug retainer section with a collection needle section. The purpose is to allow for skin puncture in order to access the vein for say blood collection, but not to allow the skin or tissue plug to be transferred to the blood collection bag. Furthermore, in accordance with the structure of the present invention the blood flow path is directed around the skin plug. This ensures that the flow of blood does not carry any of the skin plug material into the blood collection bag. Once the blood collection is complete and the collection needle is withdrawn from the donor, the skin plug retaining portion of the collection needle allows the phlebotomist to check for the presence of the skin plug in the retaining portion of the collection needle to insure it was not, as a whole, transferred to the blood collection bag.

As mentioned previously, the principles of the present invention are disclosed herein primarily in connection with a collection needle. However, the principles of the present invention may also be employed in connection with other types of hypodermic needles such as for penetrating various tissues to inject drugs, medicine, etc. In either case, the principles of the present invention provide for retention of the skin plug, in an integral structure, along with the enabling of fluid flow through the needle lumen.

Reference is now made to FIGS. 1 and 2. This describes a collection needle with an integral skin plug retainer. The needle structure includes a collection needle section 10 and a skin plug retainer section 20. The skin plug retainer section is disposed at the very distal end of the needle structure and is integral with the collection needle section 10.

Each of the sections 10 and 20 is of cylindrical construction. The collection needle section 10 has an inner lumen 12. Similarly, the skin plug retainer section 20 has an inner lumen 22. These lumens 12 and 22 are isolated from each other by a barrier wall 30. The very proximal end of section 10 may have a hub (not shown) which can either form part of or be adapted for attachment to a syringe or the like.

The collection needle section 10 may include stepped ends 14 that separate a smaller diameter midsection 15 from larger diameter end sections 16 and 17. The end section 17 is the same diameter as the skin plug retainer section. The outer diameter of the entire may alternatively be the same throughout the length of the needle, i.e., not stepped, depending on the particular needs of the application. The collection needle middle section 15 has four blood flow ports 18. Also illustrated by arrows 19 is the blood flow path which is noted, does not extend into the lumen 22 but instead extends about the skin plug retainer section 20 in through the ports 18 of the collection needle section.

As illustrated in the drawings, within the lumen 22 of the skin plug retainer section 20, there are a plurality of retaining ribs 24. These may each be a circular rib extending slightly into the lumen 22. The skin plug retainer section 20 also includes a tapered end 26 forming a pointed needle end at 28. Various different configurations of the piercing end of the needle structure may be employed with the concepts of the present invention.

Figure 4:
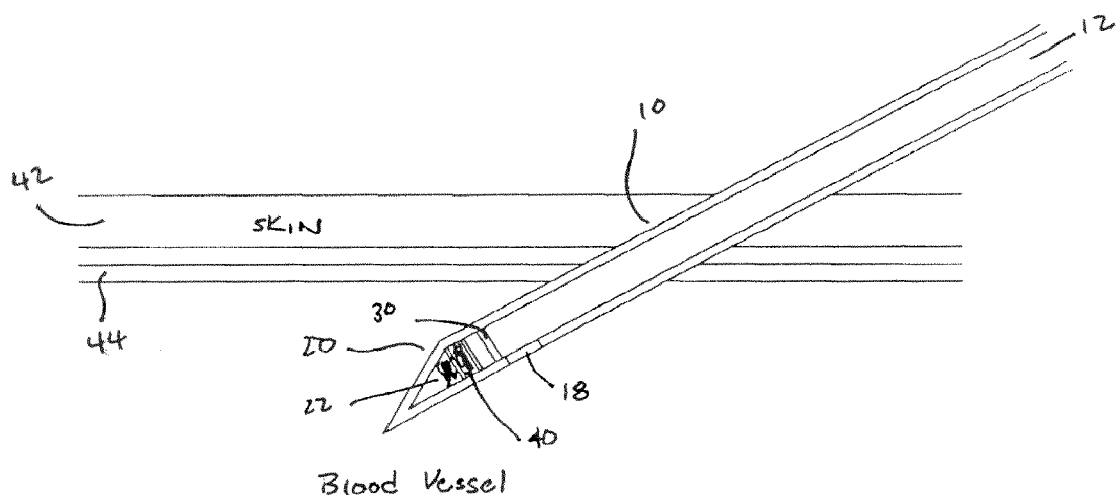
FIG. 4 illustrates the needle structure of the present invention in association with a skin layer after skin penetration.

Reference may now be made to FIGS. 3 and 4. FIG. 3 illustrates the needle structure of the present invention before skin penetration occurs. Thus, the needle structure is shown illustrated with the more distal position of the skin plug retainer section about to contact the skin layer 42. FIG. 3 also illustrates under the skin layer 42, a wall 44 of the blood vessel.

FIG. 4 illustrates the needle structure after skin penetration. Illustrated in FIG. 4 is the skin plug at 40, having been retained by the skin plug retainer section 20 as the needle penetrates the skin. This penetration is also through the blood vessel wall 44 so that blood flow may now occur, not past the skin plug, but directly about the needle through and into the lumen 12 by way of the ports 18.

Thus, there is described herein a simplified collection needle structure that has an integral skin plug retainer. This is used to retain the skin plug upon initial penetration and yet at the same time inhibit blood flow past the skin plug but enabling blood flow directly to the collection needle section through the ports 18. The barrier wall 30 prevents blood flow directly from lumen 22 to lumen 12.

Figure 5A:
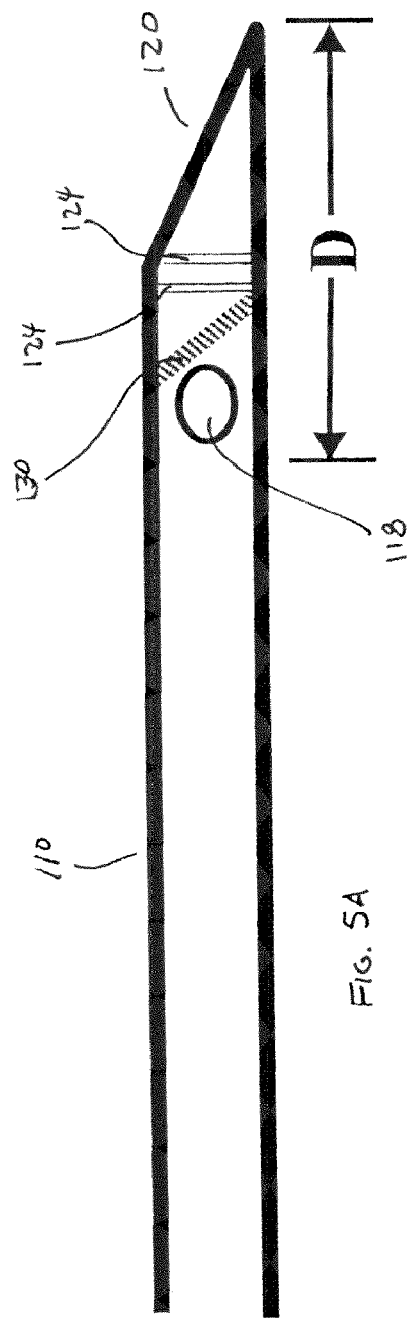
FIG. 5A illustrates a cross-sectional view of a first design of a second embodiment of a needle according to the present invention.
Figure 5B:
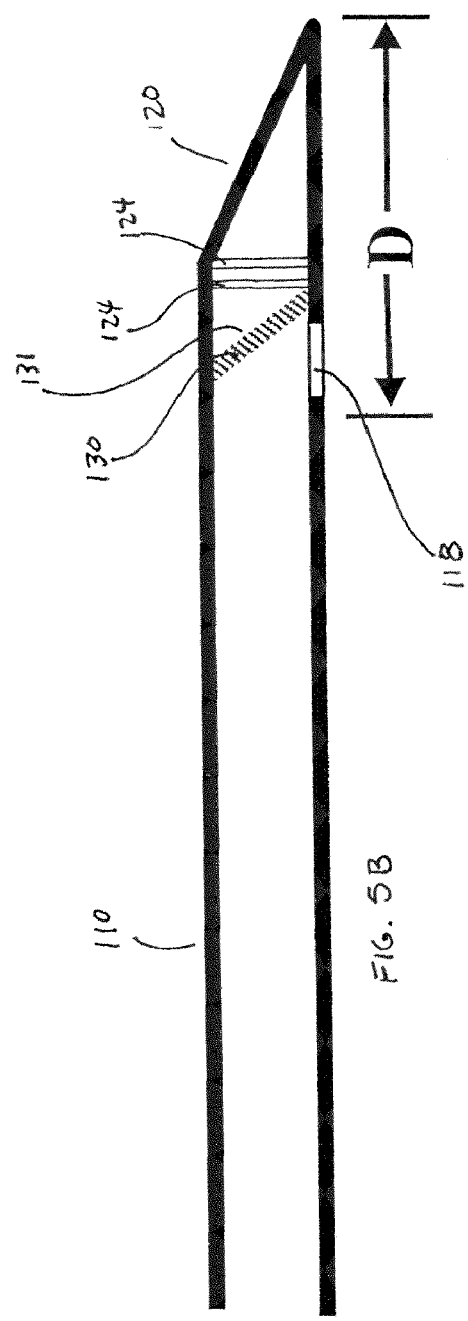
FIG. 5B illustrates a cross-sectional view of a second design of the second embodiment of the needle according to the present invention.

FIGS. 5A and 5B illustrate another embodiment of the present invention. In this embodiment, a distance "D" denotes the distance the needle must penetrate a blood vessel for proper operation. The present embodiment seeks to reduce this distance D so as to improve insertion comfort for a patient, to reduce risk of puncture through the vein during needle insertion, and to produce a needle form and operation which is substantially closer in design to a standard end flow needle.

Accordingly, as shown in FIG. 5A, the needle structure according to the present embodiment includes a collection needle section 110 and a skin plug retainer section 120. The skin plug retainer section is disposed at the very distal end of the needle structure and is integral with the collection needle section 110. Port 118 is positioned adjacent a barrier wall 130, in an effort to minimize distance D. Skin plug retaining ribs 124 may also be included Similarly, as shown in FIG. 5B, port 118 is positioned immediately adjacent side 131 of barrier wall 130, thus, further lessening distance D.

Accordingly, the positioning of the barrier wall as illustrated in FIGS. 5A and 5B decreases the insertion distance D, so that insertion comfort to the patient is enhanced, and the risk of vein puncture is reduced.

FIGS. 6A and 6B illustrate yet another embodiment of the present invention, which is directed to cutting a clean skin plug so as to also reduce insertion distance D. Specifically, as shown in FIG. 6A, the beveled end 220 of the needle 210 uses multiple and/or an all-around cutting edge. As a result, insertion distance D is reduced since the beveled end need not have a dramatic bevel.

Having now described a limited number of embodiments of the present invention, it should now be apparent to those skilled in the art that numerous other embodiments and modifications thereof are contemplated as following within the scope of the present invention. For example, one particular needle structure is shown, but it is understood that other forms of needle structures may also be employed. Also, the disclosed embodiment is for a collection needle but it is understood that the principles of the invention may also be applied to other needle structures whether for collection or, for example, for injection.

What is claimed is:

1. A method of injecting or collecting a fluid through the skin by means of a needle structure, comprising the steps of:
    (a) providing at the distal end of the needle structure a skin plug retaining section having a retaining lumen and that is integral with a more proximal fluid flow section having a lumen through which a fluid is enabled to flow;
    (b) penetrating the skin with the needle structure so as to capture a skin plug at the distal end of the needle structure in the skin plug retaining section; substantially concurrently with said step of penetrating, enabling the fluid flow through said fluid flow section lumen; and
    (c) blocking, via a barrier wall disposed between the skin plug retaining section and the fluid flow section lumen, fluid flow directly between the skin plug retaining section and the fluid flow section lumen, wherein the captured skin plug is not disturbed or otherwise displaced by the fluid flow.

2. A method of injecting or collecting a fluid through skin by means of a needle structure, comprising the steps of:
    (a) penetrating the skin with a distal end of the needle structure;
    (b) capturing a skin plug within a retaining lumen of the needle structure, substantially concurrently with said step of penetrating;
    (c) enabling fluid flow directly to a more proximal fluid flow section having a lumen through which a fluid is enabled to flow; and
    (d) blocking, via a barrier wall disposed between the retaining lumen and the more proximal fluid flow section, fluid flow directly between the retaining lumen and the more proximal fluid flow section, wherein the captured skin plug is not disturbed or otherwise displaced by the fluid flow.

3. A method as set forth in claim 2, further comprising penetrating a blood vessel with the distal end of the needle structure.

4. A method as set forth in claim 3, wherein enabling fluid flow further comprises enabling flow of blood into a blood collection bag, such that the blood flow does not carry any of the skin plug material into the blood collection bag.

5. A method as set forth in claim 2, further comprising the steps of:
    (e) withdrawing the distal end of the needle structure from the penetrated skin; and
    (f) checking for the presence of the skin plug within the retaining lumen of the needle structure.

6. A method as set forth in claim 2, wherein capturing a skin plug comprises frictionally engaging the skin plug within a retaining lumen of the needle structure.

7. A method as set forth in claim 6, wherein frictionally engaging comprises engaging the skin plug with at least some of a plurality of retaining ribs disposed within the retaining lumen of the needle structure.

8. A method as set forth in claim 2, wherein penetrating the skin comprises cutting a clean skin plug using a beveled end of the needle structure.

9. A method as set forth in claim 1, further comprising penetrating a blood vessel with the needle structure.

10. A method as set forth in claim 1, wherein enabling the fluid flow further comprises enabling flow of blood into a blood collection bag, such that the blood flow does not carry any of the skin plug material into the blood collection bag.

11. A method as set forth in claim 1, further comprising the steps of:
    (d) withdrawing the needle structure from the penetrated skin; and
    (e) checking for the presence of the skin plug within the skin plug retaining section of the needle structure.

12. A method as set forth in claim 1, wherein capturing the skin plug comprises frictionally engaging the skin plug within the skin plug retaining section of the needle structure.

13. A method as set forth in claim 1, wherein frictionally engaging comprises engaging the skin plug with at least some of a plurality of retaining ribs disposed within the skin plug retaining section of the needle structure.

14. A method as set forth in claim 1, wherein penetrating the skin comprises cutting a clean skin plug using a beveled end of the needle structure.

* * * * *